United States Patent [19]

Vogelstein et al.

[11] Patent Number: 5,834,190
[45] Date of Patent: *Nov. 10, 1998

[54] CHROMOSOME 18Q LOSS AND PROGNOSIS IN COLORECTAL CANCER

[75] Inventors: Bert Vogelstein; Kenneth W. Kinzler, both of Baltimore; Stanley Hamilton, Lutherville, all of Md.

[73] Assignee: The Johns Hopkins Unviersity, Baltimore, Md.

[*] Notice: The term of this patent shall not extend beyond the expiration date of Pat. No. 5,702,886.

[21] Appl. No.: 593,365

[22] Filed: Jan. 29, 1996

Related U.S. Application Data

[63] Continuation of Ser. No. 318,241, Oct. 5, 1994, Pat. No. 5,702,886.

[51] Int. Cl.⁶ .............................. C12Q 1/68; C12P 19/34; C07H 21/04
[52] U.S. Cl. ........................ 435/6; 435/91.2; 536/24.33; 935/77; 935/78
[58] Field of Search ..................... 435/6, 91.2; 536/23.1, 536/24.3, 24.33; 935/77, 78

[56] References Cited

U.S. PATENT DOCUMENTS

| | | | |
|---|---|---|---|
| 5,075,217 | 12/1991 | Weber ......................................... | 435/6 |
| 5,283,171 | 2/1994 | Manos et al. ................................ | 435/5 |
| 5,380,645 | 1/1995 | Vogelstein .................................... | 435/6 |

OTHER PUBLICATIONS

Jen et al., "Allelic Loss of Chromosome 18q and Prognosis in Colorectal Cancer", *New Engl. J. Med.*, 331(4):213–221 (1994).
Offerhaus et al., "The Relationship of DNA Aneuploidy to Molecular Genetic Alterations in Colorectal Carcinoma", *Gastroenterology*, 102:1612–1619 (1992).
Kern et al., "Allelic Loss in Colorectal Carcinoma", *JAMA*, 261(21):3099–3103 (1989).
O'Connell et al., "Current Status of Adjuvant Chemotherapy for Colorectal Cancer: Can Molecular Markers Play A Role in Predicting Prognosis?" *Cancer 70*:Suppl. 1732–9 (1992).
Laurent–Puig et al., "Survival and Acquired Genetic Alterations in Colorectal Cancer", *Gastroenterology*, 102:1136–1141 (1992).
Wassenbach et al., A Second Generation Linkage Map of the Human Gene, *Nature 359*; pp. 794–801, Oct. 29, 1992.
WO9109964—Vogelstein, B., Gene Deleted in Colorectal Cancer of Humans, pp. 1–31, 11, Jul. 1991.

*Primary Examiner*—W. Gary Jones
*Assistant Examiner*—Debra Shoemaker
*Attorney, Agent, or Firm*—Banner & Witcoff, Ltd.

[57] ABSTRACT

To examine the status of chromosome 18q, polymorphic genetic markers and DNA from formalin-fixed, paraffin-embedded tumors are employed. DNA from normal tissue is used as a comparison. The status of chromosome 18q is prognostic of the survival among stage II and stage III colorectal cancer patients.

13 Claims, 5 Drawing Sheets

FIG. 2

| Chromosome 18q Markers | Genetic Distance (cM) | Markers of Chromosomal Loss | | | |
|---|---|---|---|---|---|
| | | Total Loss | Partial Loss | Distal Loss | No Loss |
| D18S71 | — | | | | |
| D18S57 | 26 | | | | |
| D18S67 | 1 | | | | |
| D18S65 | 3 | | | | |
| D18S69 | 13 | | | | |
| D18S64 | 9 | | | | |
| D18S55 | 12 | | | | |
| D18S61 | 9 | | | | |
| D18S58 | 7 | | | | |
| D18S70 | 13 | | | | |
| Total | 93 | | | | |
| Patients with Metastasis/Total | | 19/25 | 5/5 | 0/1 | 1/12 |

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Homo sapiens     ( v i i i ) POSITION IN GENOME:
        ( A ) CHROMOSOME/SEGMENT: 18q
        ( B ) MAP POSITION: D18S55

( x i ) SEQUENCE DESCRIPTION: SEQ ID NO:1:

GGGAAGTCAA ATGCAAAATC 20

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Homo sapiens     ( v i i i ) POSITION IN GENOME:
        ( A ) CHROMOSOME/SEGMENT: 18q
        ( B ) MAP POSITION: D18S55

( x i ) SEQUENCE DESCRIPTION: SEQ ID NO:2:

AGCTTCTGAG TAATCTTATG CTGTG 25

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Homo sapiens     ( v i i i ) POSITION IN GENOME:
        ( A ) CHROMOSOME/SEGMENT: 18q
        ( B ) MAP POSITION: D18S58

( x i ) SEQUENCE DESCRIPTION: SEQ ID NO:3:

GCTCCCGGCT GGTTTT 16

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (ii) MOLECULE TYPE: DNA (genomic)

(vi) ORIGINAL SOURCE:
            (A) ORGANISM: Homo sapiens (viii) POSITION IN GENOME:
            (A) CHROMOSOME/SEGMENT: 18q
            (B) MAP POSITION: D18S58

(xi) SEQUENCE DESCRIPTION: SEQ ID NO:4:

GCAGGAAATC GCAGGAACTT         20

(2) INFORMATION FOR SEQ ID NO:5:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Homo sapiens (viii) POSITION IN GENOME:
            (A) CHROMOSOME/SEGMENT: 18q
            (B) MAP POSITION: D18S61

(xi) SEQUENCE DESCRIPTION: SEQ ID NO:5:

ATTTCTAAGA GGACTCCCAA ACT         23

(2) INFORMATION FOR SEQ ID NO:6:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Homo sapiens (viii) POSITION IN GENOME:
            (A) CHROMOSOME/SEGMENT: 18q
            (B) MAP POSITION: D18S61

(xi) SEQUENCE DESCRIPTION: SEQ ID NO:6:

ATATTTTGAA ACTCAGGAGC AT         22

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Homo sapiens (viii) POSITION IN GENOME:
            (A) CHROMOSOME/SEGMENT: 18q
            (B) MAP POSITION: D18S64

(xi) SEQUENCE DESCRIPTION: SEQ ID NO:7:

AACTAGAGAC AGGCAGAA         18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Homo sapiens     ( v i i i ) POSITION IN GENOME:
        ( A ) CHROMOSOME/SEGMENT: 18q
        ( B ) MAP POSITION: D18S64

( x i ) SEQUENCE DESCRIPTION: SEQ ID NO:8:

ATCAGGAAAT CGGCACTG  18

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Homo sapiens     ( v i i i ) POSITION IN GENOME:
        ( A ) CHROMOSOME/SEGMENT: 18q
        ( B ) MAP POSITION: D18S69

( x i ) SEQUENCE DESCRIPTION: SEQ ID NO:9:

CTCTTTCTCT GACTCTGACC  20

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Homo sapiens     ( v i i i ) POSITION IN GENOME:
        ( A ) CHROMOSOME/SEGMENT: 18q
        ( B ) MAP POSITION: D18S69

( x i ) SEQUENCE DESCRIPTION: SEQ ID NO:10:

GACTTTCTAA GTTCTTGCCA G  21

CHROMOSOME 18Q LOSS AND PROGNOSIS IN COLORECTAL CANCER

This application is a continuation of application Ser. No. 08/318,241, filed Oct. 5, 1994, now U.S. Pat. No. 5,702,886.

This invention was partially supported by grants (CA-35494, CA-47527, and CA-62924) from the National Cancer Institute. The U.S. government retains certain rights in this invention.

BACKGROUND OF THE INVENTION

With about 150,000 cases and 60,000 deaths annually, colorectal cancer is one of the commonest causes of death from cancer in the United States. Currently, determining prognosis and selecting patients for postoperative adjuvant therapy rely mainly on pathological and clinical staging.[2,3] The TNM system—T for primary tumor, N for regional lymph node involvement, and M for metastases—developed by the Union Internationale Contre Cancer (UICC) is one of the two major staging systems currently in use. Patients with TNM stage I cancer (Dukes stage A: tumor confined within the bowel wall, with no lymph-node metastasis) usually have a normal life span, whereas patients with stage IV disseminated disease have a very poor survival rate. However, predicting outcome in patients with intermediate stages is difficult. Patients with stage II colorectal cancer (Dukes' stage B: tumor extending through the bowel wall, without lymph-node metastasis) have a five-year survival rate of about 70 percent, and those with stage III disease (Dukes' stage C: regional lymph-node metastasis) have a rate of only 40 to 50 percent.[4] Adjuvant therapy improves the outcome in subgroups of patients, but it leads to substantial morbidity.[5-9] Better means of formulating the prognosis in patients with colorectal cancer would improve the selection of patients for adjuvant chemotherapy and radiation therapy.

Colorectal cancers result from the accumulation of several distinct genetic alterations involving the K-ras oncogene on chromosome 12 and tumor-suppressor genes on chromosomes 5, 17, and 18.[10-12] The short arm of chromosome 17 (17p) and the long arm of chromosome 18 (18q) are frequently lost in colorectal tumors. This observation led to the discovery that inactivation of the p53 and DCC gene (located on chromosomes 17p and 18q, respectively) probably contributes to the neoplastic transformation of colorectal epithelial cells.[3,4] Although studies of the biochemical mechanisms underlying the development of colorectal cancer are just beginning, the genes involved in this process have the potential to serve as markers in diagnosis and prognosis.

We have previously shown that distant metastasis of colorectal cancer is associated with deletions of chromosomes 17p and 18q and more generally with chromosomal losses throughout the genome.[15,16] Other studies have also indicated that loss of chromosome 17p or chromosome 18q has prognostic value.[17,18] However, several problems have prevented the application of these findings in a routine clinical setting. The analyses have required fresh-frozen tissues, relatively large quantities of DNA, and special procedures to isolate cancer cells from stromal and inflammatory cells within the tumor mass. In addition, Southern blot analysis depends on the heterozygosity of restriction-fragment-length polymorphisms (RFLPs), which are often absent in the chromosomal region of interest.

Thus there is a need in the art for a test which can be used in a routine clinical setting, which does not require fresh-frozen tissues, which does not require large quantities of DNA, and which does not depend on heterozygosity of restriction-fragment-length polymorphisms.

SUMMARY OF THE INVENTION

It is an object of the invention to provide molecular genetic tests for assessing the prognosis of patients with colorectal cancer.

This and other objects of the invention are provided by one or more of the embodiments described below. The present invention provides a method of determining prognosis of patients having TNM stage II colorectal cancer. The method comprises: comparing polymorphic genetic markers on chromosome 18q in tumor tissue of the patient to genetic markers on chromosome 18q in normal tissue, in order to determine somatic loss of markers on chromosome 18q;

determining a prognosis by applying the determined somatic loss of markers on chromosome 18q in the patient to outcome data obtained on a population of patients consisting of stage II colorectal cancer patients.

In another embodiment of the invention a method of determining prognosis of patients having colorectal cancer is provided. The method comprises: amplifying polymorphic genetic markers in (a) a formalin-fixed, paraffin-embedded tumor tissue of a patient having colorectal cancer and (b) a formalin-fixed, paraffin-embedded normal tissue of said patient; comparing said amplified markers from tumor and normal tissue to determine somatic loss of said markers on chromosome 18q, somatic loss of a marker on chromosome 18q indicating a poorer prognosis for the patient.

BRIEF DESCRIPTION OF THE DRAWINGS

Neoplastic tissue and non-neoplastic control tissue were separated by microdissection of routine histopathological sections from resection specimens. Total genomic DNA was isolated from each tissue sample. The polymerase chain reaction (PCR) was used to amplify polymorphic microsatellite markers capable of distinguishing between the maternal and paternal copies of chromosome 18. Allelic loss (alleles are designated as A and B on chromosome 18) was observed as absence or a relative reduction of the PCR product corresponding to the lost chromosornal arm. (On the slide label, JHH stands for Johns Hopkins Hospital.)

Chromosome 18q markers are listed from centromere (top) to telomere (bottom). The estimates of genetic distances between each marker and the one directly above it are shown in centiMorgans (cM) and are based on recombination frequencies averaged for sex. The odds in favor of the listed order of markers relative to each other, against pairwise inversion (i.e., reversed order of the pair of markers), were greater than 1 million to 1 in every case. The extent of chromosomal loss in the tumors is indicated by the shaded area. The presence of metastases in patients was determined as previously described.[15,16] In 25 patients there was loss of all studied markers, and in 5 patients there was loss of the six most distal markers; in 1 patient the tumor had lost only the most distal marker. The DCC gene lies between markers D18S65 and D18S69.

The survival rate of patients with stage II disease was significantly better than that of patients with stage III disease (P=0.006). However, when the patients were subclassified according to their status for chromosome 18q, the survival rate of patients with stage II disease whose tumor had chromosome 18q allelic loss was similar to that of patients with stage III disease, whereas patients with stage II disease whose tumor retained both alleles of chromosome 18q had a significantly better outcome (see Table 3).

Dinucleotide-repeat assays were carried out on DNA obtained from tumor and non-neoplastic tissues of the asme histopathological section. Allelic loss of chromosome 18q was observed when one of the two alleles present in the non-neoplastic tissue (N lanes) was absent or reduced in intensity in the tumor (T lanes). The chromosome 18q markers are shown D18S58 (upper panels) and D18S61 (lower panels). The tumors in panels 2, 3, 5, 6, 8, and 9 showed chromosome 18 q loss (arrowheads), whereas those in panels 1, 4, 7, and 10 did not show loss.

DETAILED DESCRIPTION OF THE PREFERRED EMBODIMENTS

It is a discovery of the present invention that the status of chromosome 18q has strong prognostic value in patients with stage II colorectal cancer. The prognosis in patients with stage II cancer and chromosome 18q allelic loss is similar to that in patients with stage III cancer, who are thought to benefit from adjuvant therapy. In contrast, patients with stage II disease who do not have chromosome 18q allelic loss in their tumor have a survival rate similar to that of patients with stage I disease and may not require additional therapy.

In addition, it is a discovery of the present invention that polymorphic genetic markers can be amplified from standard formalin-fixed, paraffin-embedded tumor tissue and that the amplifications are sufficiently quantitative so that loss of the markers can be observed. Moreover, it has been found that a small number of markers will provide informative data (i.e., heterozygosity) for a very high proportion of tumor samples. These findings make possible the application of a test for chromosome 18q loss to routine clinical situations.

Suitable polymorphic genetic markers on chromosome 18q for testing may be restriction fragment length polymorphisms (RFLPs), variable number of tandem repeats (VNTRs), microsatellites, or other polymorphic markers. They may be assayed by any means known in the art, including but not limited to polymerase chain reaction (PCR), and allele-specific ligase reaction. Suitable tumors for testing are any which demonstrate loss of chromosome 18q. These include tumors of the breast, pancreas, uterus, colon, rectum, stomach, esophagus, prostate, and blood.

Figure 1:
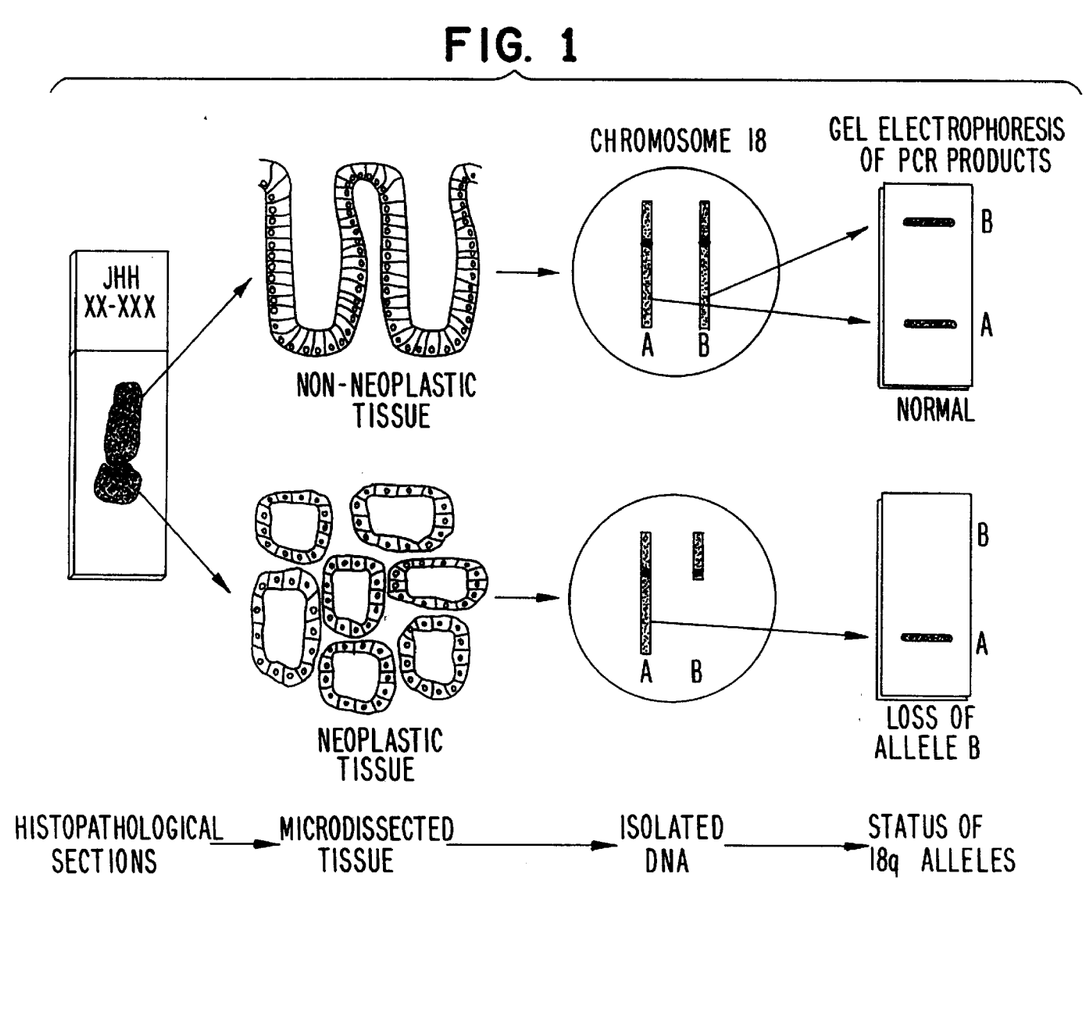
FIG. 1. Strategy for Determining the Allelic Status of the Long Arm of Chromosome 18.

To develop a practical molecular genetic test for assessing the prognosis of patients with colorectal cancer, we used formalin-fixed paraffin-embedded sections as a source of DNA and highly polymorphic microsatellite markers to determine the status of chromosome 18q. Microsatellite markers are short-tandem-repeat DNA sequences located throughout the genome.[19] They are readily assayed by polymerase-chain-reaction (PCR) amplification of small amounts of DNA and gel electrophoresis.[20-22] The two allelic forms of the microsatellites in normal cells, one inherited from each parent, migrate on gel electrophoresis as two bands of nearly equal intensity but different sizes. Chromosomal losses in tumor tissues cause a loss of one of the two PCR products or a change in their relative intensities (FIG. 1). We used this technique to determine that chromosome 18q loss is a prognostic marker in colorectal cancer.

PATIENTS

One hundred forty-five samples of stage II or III sporadic colorectal carcinoma were obtained for evaluation of the loss of chromosome 18q. They were obtained consecutively from curative surgical resections of primary colorectal tumor performed at the Johns Hopkins Hospital between July 1986 and December 1990. This period was studied because postoperative adjuvant chemotherapy was not administered routinely to patients at this institution until 1991. The tumor stage was based on pathological and clinical evaluation, which included preoperative radiography, computed tomography, and abdominal exploration at laparotomy.

Patients were excluded from the analysis if they had evidence of hereditary non-polyposis colorectal cancer syndrome according to the criteria of the International Collaborative Group,[23] had malignant tumor outside the colon within the previous five years, had synchronous adenocarcinoma of the large bowel, had carcinoma associated with idiopathic inflammatory bowel disease, or had received preoperative radiation or chemotherapy. Follow-up was carried out through the Johns Hopkins Tumor Registry and was based on chart reviews and yearly contacts with the physician or patient. Follow-up findings were confirmed in all patients as of September 1993. The clinical and pathological characteristics of the tumors were determined by a gastrointestinal pathologist without knowledge of the status of chromosome 18q, according to conventional criteria.[24]

TISSUE AND DNA PREPARATION

In the pilot study for development of the method, DNA was prepared from microdissected cryostat sections of frozen tumor tissues as previously described.[10] For the prospective study, DNA was purified with modified methods for assessing allelic loss with PCR.[25, 26] Tissue sections 6 $\mu$m thick were obtained from surgical specimens that had been fixed in formalin and embedded in paraffin for routine histopathological examination. The slides were stained with hematoxylin and eosin, dehydrated in graded ethanol, and then dried without a cover glass. Regions containing at least 70 percent neoplastic cells were inked with a black marker (Sharpie, Sanford Corp., Bellwood, Ill.) under a dissection microscope. The black marking ink increased the density of the tissue and kept it at the bottom of the tube after centrifugation. Tissues from 2 to 10 slides, each containing a blackened region of tumor 0.2 to 1 cm$^2$ in area, were scraped off with a razor blade and transferred to a 1.5 ml Microfuge tube. Non-neoplastic tissue from the same slide was then marked and placed in another Microfuge tube. The collected tissue samples were deparaffinized in 400 $\mu$l of xylene for 15 minutes and pelleted by centrifugation at 10,000×for 2 minutes. After the xylene was removed by pipette, the tissues were heated at 58° C. for 15 minutes to remove the remaining xylene and incubated overnight at 58° C. in a buffer containing 0.5M TRIS (pH 8.9), 20 mM EDTA, 10 mM sodium chloride, 0.5 mg of proteinase K per milliliter, and 1 percent sodium dodecyl sulfate. The samples were boiled in a water bath for 10 minutes at 100° C., cooled to room temperature, and then extracted twice with an equal volume of phenol and chloroform, as previously described.[27] DNA was precipitated with ethanol and dissolved in 30 $\mu$l of buffer containing 3 mM TRIS (pH 7.5) and 0.3 mM EDTA.

MICROSATELLITE MARKERS AND PCR AMPLIFICATION

Oligonucleotide primers for microsatellite markers from the long arm of chromosome 18 were designed on the basis of published sequences.[28] The following dinucleotide-repeat markers and primers were used in the prospective study: D18S55(SEQ ID NOS. 1 and 2), 5'GGGAAGTCAAATG-CAAAATC3' and 5'AGCTTCTGAGTAATCTTATGCT-GTG3'; D18S58, (SEQ ID NOS. 3 and 4) 5'GCTCCCG-GCTGGTTTT3' and 5'GCAGGAAATCGCAGGAACTT3'; D18S61,(SEQ ID NOS. 5 and 6) 5'ATTTCTAAGAG-GACTCCCAAACT3' and 5'ATATTTTGAAACTCAG-GAGCAT3'; D18S64 (SEQ ID NOS: 7 and 8), 5'AACTA-GAGACAGGCAGAA3' and 5'ATCAGGAAATCGGCACTG3'; and D18S69, (SEQ ID NOS.: 9 and 10) 5'CTCTTTCTCTGACTCTGACC3' and 5' GACTTTCTAAGTTCTTGCCAG3'. It was important to use primers that produced a PCR product less than 180 base pairs in size, because longer fragments did not amplify consistently with DNA purified from paraffin-embedded sections. PCR-based dinucleotide-repeat assays were carried out in 96-well plates for 30 cycles; each cycle was carried out at 95° C. for 30 seconds, 50° C. for 1 minute, and 70° C. for 1 minute, with primers end-labeled with $^{32}$P-labeled ATP to a specific activity of more than $10^8$ cpm per microgram of DNA and under the PCR conditions previously described.[29] Two volumes of stop buffer (95 percent formamide, 20μM sodium hydroxide, and 0.05 percent bromophenol blue and xylene cyanate) were added at the end of the amplification, and the samples were loaded onto 7 percent polyacrylamide gels containing 32 percent formamide and 5.6M urea.[30] The relative positions of the DCC gene and other chromosome 18 markers were determined by typing CEPH (Centre d'Etude du Polymorphisme Humain) reference families 1331, 1332, 1347, 1362, and 1416 for DCC[31] and using the Clinik program of the Linkage program package[32] to compute the best placement of the gene on a fixed map.

In the pilot study, the status of chromosome 17p was analyzed in the same way as that of chromosome 18q, with the microsatellite markers D17S804, D17S786, and D17S796[28] and a marker in the p53 gene.[33]

DETERMINATION OF CHROMOSOME 18Q STATUS

We defined chromosome 18q loss as the complete or partial loss of the long arm of chromosome 18. Loss of a chromosome 18q allele in a tumor was considered to be present when the PCR assay of adjacent non-neoplastic tissue showed heterozygosity of the microsatellite markers on the long arm of chromosome 18, and the relative intensity of the two alleles in the tumor DNA differed from the relative intensity in the non-neoplastic tissue DNA by a factor of at least 1.5.[34] When the loss of the allele was not obvious on visual inspection, the intensities of the bands were quantitated with a Phosphorlmager (Molecular dynamics, Sunnyvale, Calif.). Some tumors (6 of 43 in the pilot study and 18 of 137 in the prospective study) yielded PCR products of abnormal sizes with two or more microsatellite markers. These tumors were considered to be in the previously described replication error (RER) subclass.[35-3] It is difficult to ascertain allelic loss of chromosome 18q with microsatellite markers in RER-positive tumors because of the instability of the repeats. However, such tumors infrequently lose any chromosomes, including chromosome 18q.[37] In the pilot study reported here, Southern blot analysis showed that none of the RER-positive tumors had lost chromosome 18q.[39] Therefore, tumors of the RER type were included among the tumors with no loss of chromosome 18q in the survival and other statistical analyses.

In the prospective study, two dinucleotide-repeat markers from chromosome 18q (D18S61 and D18S58) were sufficient to determine the status of the chromosome in 110 of the 135 paraffin-embedded tumor specimens (81 percent). Additional markers (D18S69, D18S64, and D18S55) were required only when no heterozygosity in either D18S61 or D18S58 was present in the non-neoplastic tissue, or when atypical bands indicating a potential RER phenotype were observed in either marker.

STATISTICAL ANALYSIS

The primary statistical outcome in this study was overall survival measured from the date of surgery. Event-time distributions were estimated with the product-limit method.[40] Differences between prognostic factors were tested for statistical significance with the log-rank statistic.[41] More generally, we estimated the hazard (risk) ratio per unit of change in each level of a potential prognostic factor relative to a specific base-line level. For example, the risk of death among patients with chromosome 18q loss was compared with the risk among patients with no loss, for all follow-up time and all patients. For prognostic factors that were continuous variables (e.g., tumor size), the risk ratio was expressed per unit of change (e.g., per centimeter of increase in size). Hazard ratios and associated 95 percent confidence intervals were estimated with the proportional-hazards model.[42] All reported P values are two-sided.

The simultaneous effects of more than one prognostic factor were estimated by multiple regression in the proportional-hazards model.[42] In this analysis, all factors that were potentially prognostic when considered alone (i.e., the P value was less than 0.15) were entered into a multiple regression model from which hazard ratios and significance levels were estimated. A factor that was not statistically significant or that had an estimated hazard ratio near 1.0 was removed from the model. Hazard ratios and significance levels were then estimated again to derive a more parsimonious model. This step-down procedure was continued until all remaining factors were significant. In some cases, we retained factors that were not significant solely to illustrate their lack of effect in the presence of other factors. In addition, the effects of prognostic factors were controlled by stratified proportional-hazards regression (e.g., rectal vs. colonic tumors) to avoid the assumption of proportional hazards.

MICROSATELLITE MARKERS FOR CHROMOSOME 18Q ALLELIC LOSS

To establish the reliability of dinucleotide-repeat $((CA)_n)$ markers for determining chromosomal loss, we tested 43 pairs of tumor and non-neoplastic DNA samples from fresh-frozen tissues in a pilot study. The chromosomal status of 36 of these tumors had been analyzed in detail by hybridizing Southern blots with DNA probes capable of detecting RFLPs of chromosome 18q.[39] Ten dinucleotide-repeat markers spanning the entire length of chromosome 18q were used to assess the loss of genetic material in this chromosomal region of the tumors. The results obtained with the dinucleotide-repeat assays corresponded perfectly to the available data on RFLPs. Twenty-seven tumors in which Southern blot analysis showed total or partial loss of chromosome 18q had similar losses according to the $(CA)_n$-repeat assay, and nine tumors that showed no loss of RFLP markers on Southern blot analyses also retained all informative $(CA)_n$ markers. The status of chromosome 18q in the remaining seven tumors (16 percent) was determined with use of $(CA)_n$ markers (four of the tumors had loss of chromosome 18q, and three had no loss), but no comparison with Southern blot data was possible because of the lack of informative RFLP markers in these tumors.

Figure 2:
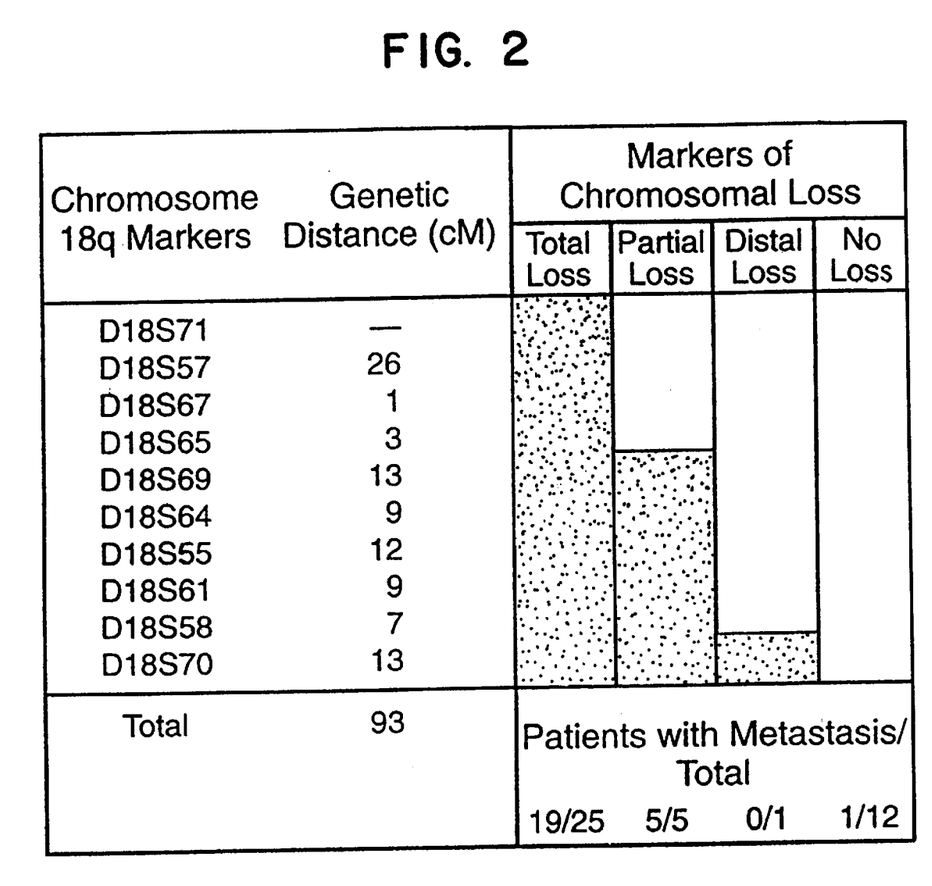
FIG. 2. Chromosome 18q Markers and Their Association with Metastasis in the Pilot Study.

We then examined the association between the region of chromosome 18q that was lost and the presence of metastasis in the 43 patients, all of whom had been followed at least five years (FIG. 2). Metastases were found in 19 of the 25 patients whose tumors had lost all the markers studied and all 5 patients with loss of the six most distal markers but not markers more proximal. In contrast, the 1 patient whose tumor had lost only the most distal marker (D18S70) and 11 of 12 patients whose tumor had not lost any marker were free of metastasis. Thus, the dinucleotide markers D18S69, D18S64, D18S55, D18S61, and D18S58 (FIG. 2) were most closely associated with the presence of metastatic disease. The markers were found to be highly polymorphic and produced robust signals in the PCR-based dinucleotide-repeat assay.

In this pilot study we also assessed the loss of chromosome 17p with four microsatellite markers. There was a strong concordance between chromosome 17p and chromosome 18q allelic losses (35 of 43 tumors), as in our previous study,[15,16] but chromosome 18q allelic loss was more closely associated with metastasis in patients whose tumor had either chromosome 17p or chromosome 18q allelic loss. All three patients whose tumor had chromosome 18q allelic paraffin-embedded tumor sections coincided precisely with the results obtained with DNA from cryostat sections of the same frozen tumors (data not shown).

CLINICAL CHARACTERISTICS ASSOCIATED WITH CHROMOSOME 18Q ALLELIC LOSS

Figure 4:
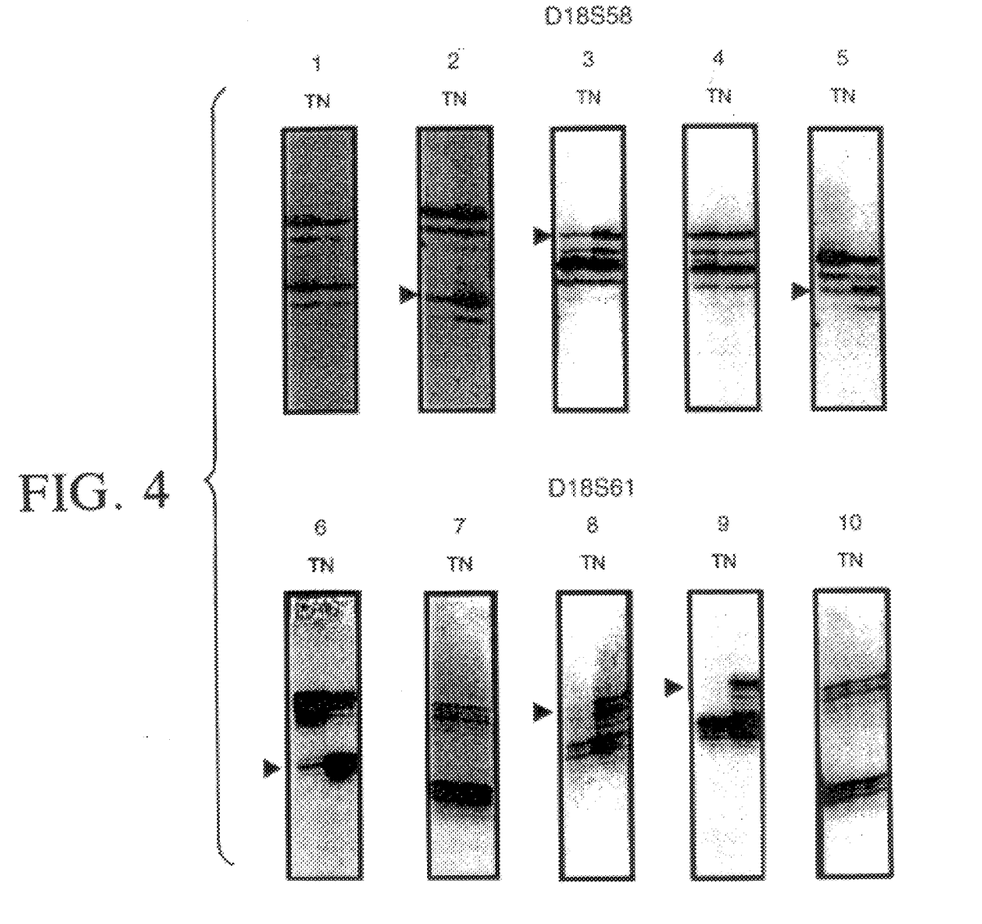
FIG. 4. Chromosome 18q Allelic Loss in DNA from Formalinin-Fixed Paraffin-Embedded Tumor Sections.

We used this dinucleotide-repeat assay to evaluate consecutively resected tumors from a cohort of 145 patients. We were able to determine the status of chromosome 18q in 135 of the 145 tumor specimens (93 percent); 6 specimens were not analyzed because of insufficient amounts of tumor or non-neoplastic tissue, and 4 specimens could not be analyzed because of failed PCR amplifications. Table 1 lists relevant clinical characteristics of all 145 patients and the 135 patients whose tumors were analyzed for chromosome 18q allelic loss. Of the 135 tumors we studied, 90 (67 percent) had either complete or partial loss of chromosome 18q (examples are shown in FIG. 4). Fewer patients with stage II disease had chromosome 18q allelic loss in their tumor than the patients with stage III disease (P=0.007). More than two thirds of the tumors with chromosome

TABLE 1

Clinical Characteristics of All Patients with Colorectal Cancer and Patients Whose Tumors Were Evaluated for Chromosome 18 q Status.

| VARIABLE | CATEGORY | ALL PATIENTS (N = 145) no. | PATIENTS EVALUATED (N = 135) | | P VALUE* |
|---|---|---|---|---|---|
| | | | NO 18 q LOSS no. (%) | 18 q LOSS | |
| Sex | Male | 74 | 20 (44) | 48 (53) | NS |
| | Female | 71 | 25 (56) | 42 (47) | |
| Race | White | 103 | 35 (78) | 62 (69) | NS |
| | Other† | 42 | 10 (22) | 28 (31) | |
| Mean age ± SD - yr | | 65.3 ± 12.7 | 65.1 ± 15.6 | 65.8 ± 10.9 | NS |
| Tumor Site | Rectum | 27 | 5 (11) | 20 (22) | NS |
| | Colon | 118 | 40 (89) | 70 (78) | |
| TNM stage | II | 69 | 29 (64) | 36 (40) | 0.007 |
| | III | 76 | 16 (36) | 54 (60) | |
| Tumor side‡ | Right | 59 | 31 (69) | 26 (29) | <0.001 |
| | Left | 86 | 14 (31) | 64 (71) | |
| Tumor differentiation | Well | 14 | 6 (13) | 8 (9) | |
| | Moderate | 109 | 26 (58) | 74 (82) | 0.005 |
| | Poor | 22 | 13 (29) | 8 (9) | |
| Adjuvant therapy | Yes | 34 | 5 (11) | 25 (28) | 0.026 |
| | No | 111 | 40 (89) | 65 (72) | |
| Vital status | Alive | 96 | 37 (82) | 52 (58) | 0.005 |
| | Dead | 49 | 8 (18) | 38 (42) | |
| Mean follow-up ± SD - mo | | 35.4 ± 16.9 | 38.7 ± 17.6 | 33.1 ± 16.4 | NA |

*A chi-square test of equality was used in comparison of variables that had two categories, and a test of homogeneity was used in the comparison of the one variable with three categories and a test of homogeneity was used in the comparison of the one variable with three categories (tumor differentiation).
NS denotes not significant, and
NA not applicable.
†This category contained 40 black patients, 1 Asian patient, and 1 Hispanic patient.
‡The tumor side was based on the position of the tumor relative to the splenic flexure.

loss but not chromosome 17p allelic loss had metastatic disease, whereas only one of five patients with chromosome 17p allelic loss but not chromosome 18q allelic loss had metastases. Therefore, the chromosome 18q markers were chosen for the subsequent prospective study. FIG. 2 shows the relative chromosomal position and genetic distance of these 10 dinucleotide-repeat markers.

Using five chromosome 18q markers, we tested the applicability of the dinucleotide-repeat assay to DNA from formalin-fixed paraffin-embedded tumor specimens in the pilot study (FIG. 4). The results of the assays with 17 18allelic loss were in the patient's left colon (i.e., distal to the splenic flexure), whereas two thirds of the tumors without chromosome 18q allelic loss were on the right (P<0.001). The frequency of 18q allelic loss among patients with colon cancers was not significantly different from the frequency among those with rectal cancers (P=0.12). Patients receiving adjuvant therapy were more common in the group with chromosome 18q allelic loss (P=0.026) because adjuvant therapy was given more frequently for stage III cancer than for stage II cancer (28 of 76 patients and 6 of 69 patients, respectively). At the close of this study, 83 percent of the patients without chromosome 18q allelic loss and 58 percent of the patients with chromosome 18q allelic loss were still alive at the time of the last follow-up evaluation (P=0.005). The mean follow-up time was 33 months in the patients with chromosome 18q allelic loss and 38 months in those without such loss.

STATUS OF CHROMOSOME 18Q AND SURVIVAL

Figure 3A:
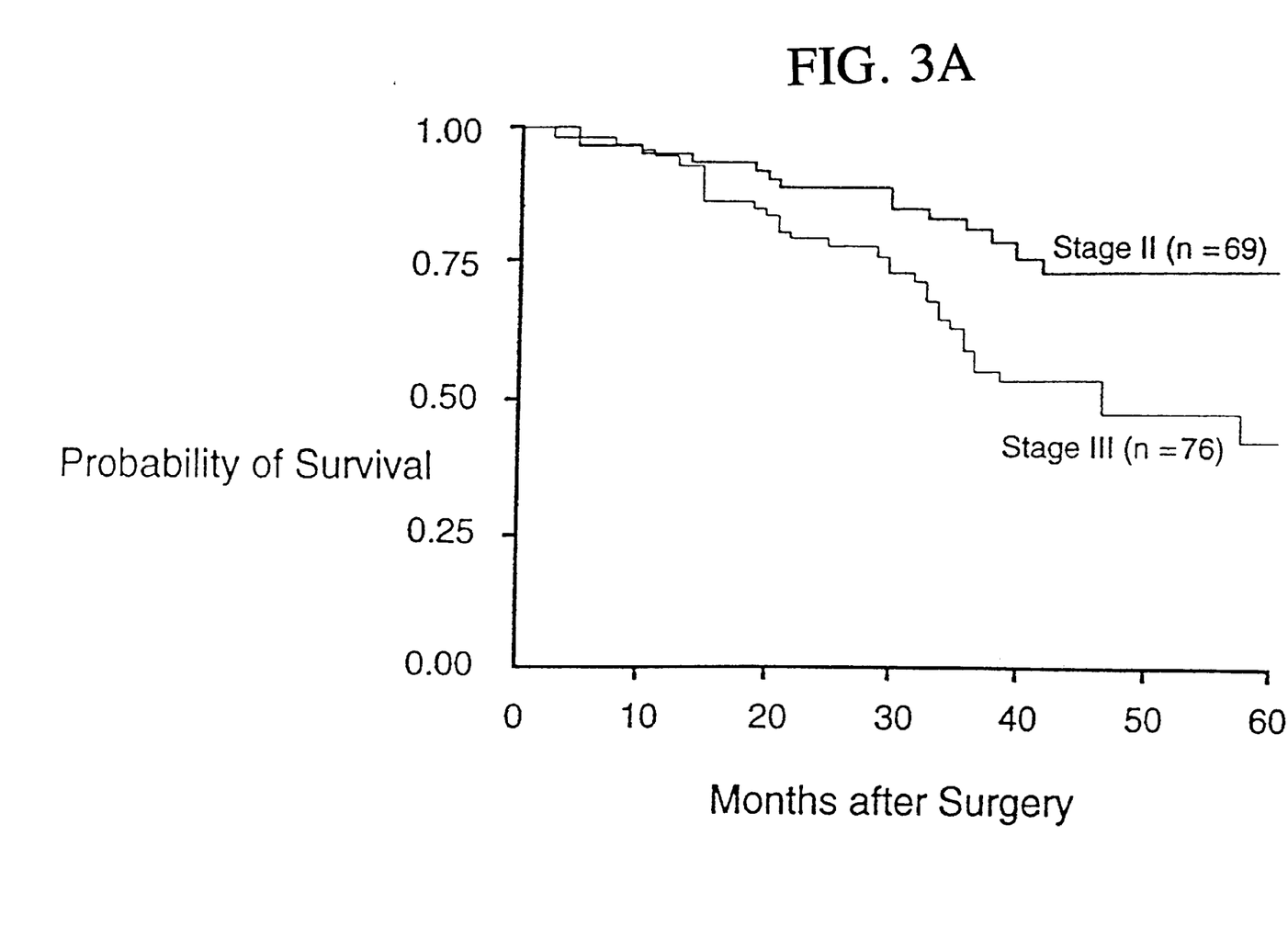
FIG. 3A and 3B. Overall Survival of Patients with Colorectal Cancer, According to TNM Stage Alone (Panel A) and Both TNM Stage and Chromosome 18q Allelic Loss (Panel B).
Figure 3B:
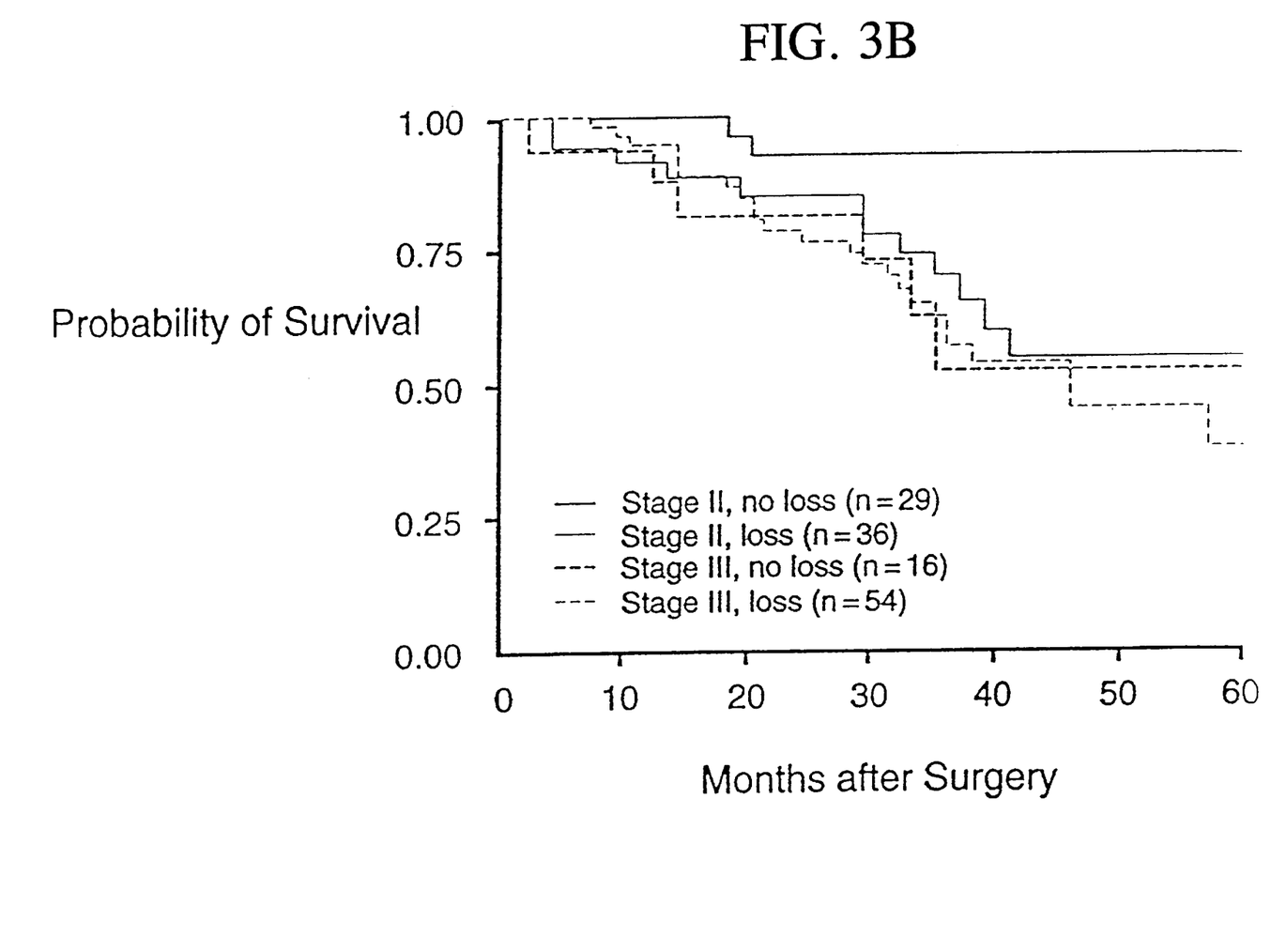

Clinical stage was a significant prognostic factor for survival (FIG. 4A). In this cohort of patients the overall five-year survival rate was 74 percent in those with stage II disease and 42 percent in those with stage III disease. However, when the status of chromosome 18q was considered, the five-year survival rate was 93 percent in patients with stage II disease whose tumor had no chromosome 18q allelic loss and 54 percent in patients in the same stage whose tumor had chromosome 18q allelic loss (FIG. 3A and 3B). The survival rate in the latter group of patients did not differ significantly from the survival rate among patients with stage III tumors. The survival rate among patients with stage III colorectal cancer was independent of their status for chromosome 18q. Similar results were obtained when disease-free survival was the end point and when colonic and rectal tumors were analyzed independently. Adjuvant therapy had no significant effect on the outcome in this study (Table 2).

CHROMOSOME 18Q ALLELIC LOSS AND OTHER PROGNOSTIC FACTORS

Besides chromosome 18q allelic loss, other factors were associated with a higher or lower risk of death when these factors were considered individually. Chromosome 18q allelic loss, advanced tumor stage, extramural vein invasion, perineural invasion, and poor tumor differentiation were all associated with a significantly poorer prognosis, whereas white race and female sex were associated with a better prognosis (Table 2). However, as is frequently the case in such analyses, there were correlations among the various prognostic factors we analyzed. As examples, patients in an advanced stage of disease had a higher frequency of poorly differentiated tumors, and poorly differentiated tumors were more likely to involve veins and nerves. In such situations, individual factors are only partially independent with respect to their ability to predict survival.

To study the independent effects of the prognostic factors in the presence of correlations, we used a multiple regression proportional-hazards model. Table 3 shows three representations of multiple regression models. The first model illustrates the fit of a roughly optimal set of prognostic factors in the cohort of patients—that is, the addition of any other recorded variable did not yield prognostic information independent of the information produced by the factors listed. It is noteworthy that in patients whose tumor had chromosome 18q allelic loss, the risk of death was more than doubled, even after adjustment for vein involvement, grade of tumor differentiation, and race (Table 3, model 1). When the TNM stage was added to this set of predictors, this factor seemed to be

TABLE 2

Estimated Hazard Ratios for
Selected Individual Prognostic Factors in All 145 Patients Studied.

| FACTOR | CATEGORY | HAZARD RATIO | 95% CONFIDENCE INTERVAL | P VALUE* |
|---|---|---|---|---|
| Chromosome 18 q | Loss vs. no loss | 2.83 | 1.32–1.08 | 0.008 |
| TNM stage | III vs. II | 2.33 | 1.27–4.28 | 0.006 |
| Vein invasion | Yes vs. no | 3.29 | 1.83–5.91 | <0.001 |
| Perineural invasion | Yes vs. no | 3.08 | 1.73–5.48 | <0.001 |
| Tumor differentiation | Moderate vs. well | 2.43 | 0.57–10.3 | 0.24 |
| | Poor vs. well | 4.28 | 0.94–19.4 | 0.06 |
| Race | White vs. other† | 0.61 | 0.34–1.10 | 0.10 |
| Sex | Male vs. female | 1.30 | 0.74–2.29 | 0.36 |
| Tumor side‡ | Left vs. right | 1.63 | 0.87–3.05 | 0.13 |
| Tumor site | Colon vs. rectum | 0.83 | 0.41–1.66 | 0.59 |
| Adjuvant therapy | Yes vs. no | 0.74 | 0.40–1.38 | 0.34 |

*P values result from a test of the hypothesis that the hazard ratio equals 1.0.
†The "other" category contained 40 black patients, 1 Asian patient, and 1 Hispanic patient.
‡The tumor side was based on the position of the tumor relative to the splenic flexure.

TABLE 3

Hazard Ratios for
Prognostic Factors in Multiple Regression Modes Including All 145 Patients.

| FACTOR* | CATEGORY | HAZARD RATIO | 95% CONFIDENCE INTERVAL | P VALUE† |
|---|---|---|---|---|
| Model 1 | | | | |
| Chromosome 18 q | Loss vs. no loss | 2.46 | 1.06–5.71 | 0.036 |
| Vein invasion | Yes vs. no | 2.64 | 1.38–5.08 | 0.004 |
| Tumor differentiation‡ | Test of trend | 2.80 | 1.41–5.54 | 0.003 |
| Race | White vs. other§ | 0.44 | 0.23–0.83 | 0.011 |
| Model 2 | | | | |

TABLE 3-continued

Hazard Ratios for
Prognostic Factors in Multiple Regression Modes Including All 145 Patients.

| FACTOR* | CATEGORY | HAZARD RATIO | 95% CONFIDENCE INTERVAL | P VALUE† |
|---|---|---|---|---|
| Chromosome 18 q | Loss vs. no loss | 2.48 | 1.05–5.84 | 0.038 |
| Vein invasion | Yes vs. no | 2.67 | 1.32–5.40 | 0.006 |
| Tumor differentiation‡ | Test of trend | 2.81 | 1.41–5.62 | 0.003 |
| Race | White vs. other§ | 0.44 | 0.23–0.83 | 0.011 |
| TNM stage | III vs. II | 0.97 | 0.48–1.97 | 0.927 |
| Model 3 | | | | |
| Chromosome 18 q | Loss vs. no loss | 3.32 | 1.43–7.73 | 0.005 |
| Tumor differentiation‡ | Test of trend | 2.89 | 1.43–5.81 | 0.003 |
| Race | White vs. other§ | 0.42 | 0.22–0.80 | 0.008 |
| TNM state | III vs. II | 1.40 | 0.73–2.68 | 0.307 |

*The effects of prognostic factors are considered jointly in each multiple regression model.
†P values result from a test of the hypothesis that the hazard ratio equals 1.0.
‡The effect of differentiation was modeled as a trend - i.e., the effect of moderately differentiated tumors as compared with well-differentiated tumors was assumed to be the same as the effect of poorly differentiated tumors as compared with moderately differentiated tumors.
§The "other" category contained 40 black patients, 1 Asian patient, and 1 Hispanic patient.

redundant (i.e., it did not provide additional prognostic—information) in the group studied, which consisted of patients with stage II and stage III disease only (Table 3, model 2). The factors that were redundant with TNM stage were not easily identifiable, but when vein invasion was removed from the regression model, the estimated hazard ratio for TNM stage increased (Table 3, model 3); retention of either tumor differentiation or vein involvement decreased the estimated prognostic effect of TNM stage. In contrast, the significance of chromosome 18q allelic loss as a prognostic factor remained nearly the same despite the inclusion of other factors in the regression analysis. Furthermore, when those models were stratified according to tumor site (colon vs. rectum), the estimated hazard ratios, P values, and confidence intervals were essentially unchanged.

These results demonstrate that chromosome 18q allelic loss is an important prognostic marker in patients with stage II colorectal cancer. The subgroup of all patients with stage II disease whose tumor had retained both alleles of chromosome 18q (45 percent of all these patients) had an excellent outcome (five-year survival of 93 percent), whereas survival in patients with stage II disease whose tumor had lost one allele of chromosome 18q was similar to that in patients with stage III disease (five-year survival of 54 percent) (FIG. 4B). Although the majority of the patients we studied had colon cancer, our results suggest that the prognostic value of allelic loss of chromosome 18q also pertains to rectal cancer. Our study suggests that adjuvant therapy with levamisole and fluorouracil, which reportedly benefits patients with stage III disease,[8] may also be appropriate for patients with stage II disease whose colonic tumors have lost chromosome 18q.

Patients with stage III disease had a significantly higher frequency of chromosome 18q allelic loss than did those with stage II disease (77 percent vs. 55 percent) (Table 1), but chromosome 18 q allelic loss had no significant prognostic value in patients with stage III disease. This finding may relate to the complexity of the metastatic process; allelic loss of chromosome 18 q is clearly not a prerequisite for metastasis in colorectal cancer. It is thus possible that some stage III tumors have a worse prognosis through pathways that do not involve chromosome 18 q.

In addition to the status of chromosome 18 q, several conventional factors also had prognostic value in our study. These included invasion of extramural veins by tumor cells, perineural invasion, and poor tumor differentiation. These factors, however, can vary considerably within the same tumor and can be perceived differently from observer to observer.

Rapid advances in the molecular genetics of colorectal cancer have stimulated attempts to use molecular markers for assessing prognosis in patients with this disease. Altered total DNA content (aneuploidy), assessed by flow cytometry, can correlate with advanced tumor stage, poor tumor differentiation, and relatively poor survival,[43] but the technical difficulties of flow cytometry have led to conflicting results.[44,45] Fractional allelic loss, assayed by Southern blot analysis, has been used as a measure of chromosomal loss throughout the genome.[15,16,39] High fractional allelic loss is associated with poor survival, but the large number of chromosomal sites needed for analysis renders the method impractical for routine use.

Microsatellite instability, a manifestation of the RER phenotype, has been described in sporadic colorectal carcinomas[24,35,36] and hereditary non-polyposis colorectal cancer.[37,38] In our study, the five-year survival rate of the 18 patients with RER-positive tumors was indistinguishable from that of the 28 patients whose tumors had retained chromosome 18q and were RER-negative. These results agree with other reports that RER-positive tumors have a lower tendency to metastasize than RER-negative tumors and that patients with RER-positive tumors have relatively good survival.[35,37] Our pilot study showed that RER-positive tumors do not often lose any allele of chromosome 18q. It is possible that the better outcome in patients with RER-positive tumors is a result of retention of both alleles of chromosome 18q.

Certain specific genetic alterations have also been studied as potential prognostic markers. Activating mutations of ras proto-oncogenes and loss of the nm23 gene have been reported to have prognostic importance.[46-48] One of the most commonly affected genes in human cancers is p53.[49,50] Mutational inactivation of the p53 gene often accompanies the loss of chromosome 17 p, and accumulation of the mutated protein occurs frequently in colorectal cancers.[13,49] Such mutation or loss of p53 has made it potentially useful for diagnosis and prognosis.[15-18,50-53] In our pilot study, chromosome 17 p allelic loss was less closely associated with metastasis than chromosome 18 q allelic loss. In our prospective study, overexpression of p53, as assessed by immunohistochemical analysis, was not useful for determining prognosis.

Study of the commonly deleted regions on chromosome 18q led to the identification of the candidate tumor-suppressor genie DCC (deleted in colorectal The DCC protein has structural features in common with certain types of cell-adhesion molecules and may participate with other proteins in cell-cell and cell-matrix interactions.[14,54–56] The loss of chromosome 18 q could thus lead to impaired contacts between cells, thereby contributing to tumor growth and invasion. Linkage analysis indicates that the DCC gene lies immediately adjacent to the region of chromosome 18 q that we evaluated in our prospective study (between D18S69 and D18S65) (FIG. 2). Interestingly, expression of the DCC gene was recently shown to be absent in most colorectal cancers that were metastatic to the liver, but it was lost only in a minority of nonmetastatic cancers.[57] This finding supports the idea that the DCC gene is the biologic basis of the association of chromosome 18 q with prognosis. However, an additional gene (or genes) on chromosome 18 and elsewhere in the genome may also play a part, and further biochemical and genetic studies are required.

The prognostic evaluation afforded by the chromosome 18 q assay is clinically meaningful but imperfect. Although retention of chromosome 18 q is a favorable finding, the outcome in patients whose tumor has chromosome 18 q allelic loss is unpredictable, and the prognosis of patients with stage III disease is unchanged by knowledge of the status of chromosome 18 q. In the future, tests for the status of chromosome 18 q may be combined with other genetic and biochemical assays to improve prognostic evaluation in patients with colorectal cancer.

The following articles are incorporated herein by reference.

REFERENCES

1. Cancer facts & figures—1993, *Atlanta: American Cancer Society*, 1993.
2. *JAMA*, 1990, 264:1444–50.
3. Deans, et al., *Br. J. Surg.*, 1992, 79:608–13.
4. Crissman, et al., Pathologic staging of colon and rectal adenocarcinoma, In: *Colorectal cancer*, Wanebo, H. J., ed., St. Louis: Mosby—Year Book, 1993, pp. 57–74.
5. Gastrointestinal Tumor Study Group, *N. Engl. J. Med.*, 1985, 312:146–572.
6. Douglass, et al., *N. Engl J. Med.*, 1986, 315:1294–5.
7. Laurie, et al., *J. Clin. Oncol*, 1989, 7:1447–56.
8. Moertel, et al., *N. Eng. J. Med.*, 1990, 322:352–8.
9. Krook, et al., *N. Engl. J. Med.*, 1991, 324:709–15.
10. Vogelstein, et al., *N. Engl J. Med.*, 1988, 319:525–32.
11. Fearon, et al., *Cell*, 1990, 61:759–67.
12. Hamilton, S. R., *Gastroenterology*, 1993, 105:3–7.
13. Baker, et al., *Science*, 1989, 244:217–21.
14. Fearon, et al., *Science*, 1990, 247:49–56.
15. Kern, et al., *JAMA*, 1989, 261:3099–103, [Erratum, *JAMA*, 1989, 262:1952.]
16. Offerhaus, et al., *Gastroenterology* 1992, 102:1612–19.
17. Laurent-Puig, et al., *Gastroenterology*, 1992, 102:1136–41.
18. O'Connell, et al., *Cancer*, 1992, 70:Suppl: 1732–9.
19. Beckman, et al., *Genomics*, 1992, 12:627–31.
20. Saiki, et al., *Science*, 1988, 239:487–91.
21. Louis, et. al., *Am. J. Patrol*, 1992, 141:777–82.
22. NIH/CEPH Collaborative Mapping Group, *Science*, 1992, 258:67–86.
23. Vasen, et al., *Lancet*, 1991, 338:877.
24. Kim, et al., *Am. J. Pathol.*, 1994, 145:148–56.
25. Meltzer, et al., *Proc. Natl. Acad. Sci. USA*, 1991, 88:4976–80.
26. Shibata, et al., *Am. J. Pathol*, 1992, 141:539–43.
27. Goelz, et al., *Biochem. Biophys. Res. Commun.*, 1985, 130:118–26.
28. Weissenbach, et al., *Nature*, 1992, 359:794–801.
29. Sidransky, et al., *Science*, 1992, 256:102–5.
30. Litt, et al., *Biotechniques*, 1993, 15:280–4.
31. Risinger, et al., *Hum. Mold Genet.*, 1992, 1:657.
32. Lathrop, et al., *Proc. Natl. Acad. Sci. USA*, 1984, 81:3443–6.
33. Hahn, et al., *Clin. Chem.*, 1993, 39:549–50.
34. Gruis, et al., *Br. J. Cancer*, 1993, 68:308–13.
35. Ionov, et al., *Nature*, 1993, 363:558–61.
36. Thibodeau, et al., *Science*, 1993, 260:816–9.
37. Aaltonen, et al., *Science*, 1993, 260:812–6.
38. Peltornaki, et al., *Cancer Res.*, 1993, 53:5853–5.
39. Vogelstein, et al., *Science*, 1989, 244:207–11.
40. Kaplan, et al., *J. Am. Stat. Assoc.*, 1958, 53:457–81.
41. Mantel, et al., *J. Natl. Cancer Inst.*, 1959, 22:719–48.
42. Cox, D.R., *J. R. Stat. Soc. [B]*, 1972, 34:187–220.
43. Jass, et al., *J. Clin. Pathol.*, 1989, 42:254–9.
44. Ensley, et al., *Cytometry*, 1993, 14:550–8.
45. Crissman, et al., *Pathol Annu.*, 1989, 24:103–47.
46. Finkelstein, et al., *Arch. Surg.*, 1993, 128:526–32.
47. Cohn, et al., *Lancet*, 1991, 338:722–4.
48. Bell, et al., *Gastroenterology*, 1993, 104:57–64.
49. Nigro, et al., *Nature*, 1989, 342:705–8.
50. Harris, et al., *N. Engl J. Med.*, 1993, 329:1318–27.
51. Baas, et al., *J. Pathol.*, 1994, 172:5–12.
52. Remvikos, et al., *Br. J. Cancer*, 1992, 66:758–64.
53. Hamelin, et al., *Gastroenterology*, 1994, 106:42–8.
54. Hedrick, et al., *Trends Cell Biol*, 1993, 3:36–9.
55. Nigam, et al., *Br. J. Cancer*, 1993, 68:507–14.
56. Wielenga, et al., *Cancer Res.*, 1993, 53:4754–6.
57. Zetter, B.R., *Semin. Cancer Biol*, 1993, 4:219–29.

We claim:

1. A method of determining prognosis of patients having colorectal cancer, comprising:

amplifying microsatellite markers on chromosome 18q which are between D18S69 and D18S58, inclusive, in (a) a formalin-fixed, paraffin-embedded tumor tissue of a patient having colorectal cancer and (b) a formalin-fixed, paraffin-embedded non-neoplastic tissue of said patient;

comparing said amplified microsatellite markers from tumor and non-neoplastic tissue to determine somatic loss of said microsatellite markers on chromosome 18q; and     using somatic loss of at least one of said microsatellite markers on chromosome 18q as an independent prognostic marker, wherein, if it is determined that none of said microsatellite markers are lost, then the patient has a longer predicted survival rate than if it is determined that at least one of said microsatellite markers on chromosome 18q is lost.

2. The method of claim 1 wherein the cancer is a stage II colorectal cancer.

3. The method of claim 1 wherein the microsatellite markers amplified are less than 180 bp in length.

4. The method of claim 1 wherein the microsatellite markers are selected from the group consisting of D18S69, D18S64, D18S55, D18S61, and D18S58.

5. The method of claim 1 wherein the microsatellite markers comprise D18S69, D18S64, D18S55, D18S61, and D18S58.

6. The method of claim 1 wherein the microsatellite markers comprise D18S61 and D18S58.

7. The method of claim 4 wherein the microsatellite markers are selected from the group consisting of D18S61 and D18S58.

8. The method of claim 4 wherein primers for amplifying said microsatellite markers have the sequences shown in SEQ ID NO:1–10.

9. The method of claim 1 wherein the non-neoplastic tissue was adjacent to the tumor in the patient's body.

10. A method of determining prognosis of a patient having a TNM stage II colorectal cancer, comprising:

determining the presence or absence of two or more polymorphic genetic markers on chromosomes 18q in tumor tissue of the patient, wherein the polymorphic genetic markers are between D18S69 and D18S58, inclusive;

determining the presence or absence of said two or more polymorphic genetic markers on chromosome 18q in non-neoplastic tissue of the patient; a polymorphic marker which is absent in said tumor tissue but present in said non-neoplastic tissue, indicating a somatic loss of markers on chromosome 18q; and ascertaining a predicted survival rate for the patient by applying survival outcome data obtained from a population of patients consisting of TNM stage II colorectal cancer patients in which somatic loss of said polymorphic markers on chromosome 18q has been measured and used to divide the population of patients into two groups, wherein those with a somatic loss of at least one of said polymorphic markers on chromosome 18q are in a first group and those with no somatic loss of said polymorphic markers on chromosome 18q are in a second group, wherein the survival rate of the first group is provided to the patient if the patient is determined to have a somatic loss of at least one of said polymorphic markers and the survival rate of the second group is provided to the patient if the patient is determined to have no somatic loss of said polymorphic markers, wherein somatic loss of at least one of said polymorphic markers provides an independent prognostic marker.

11. The method of claim 10 wherein the polymorphic genetic markers are microsatellite markers.

12. The method of claim 10 wherein the tissues compared are formalin-fixed, paraffin-embedded specimens.

13. The method of claim 10 wherein the polymorphic genetic markers are amplified prior to said step of comparing.

* * * * *